US012577184B2

(12) United States Patent
Janka et al.

(10) Patent No.: US 12,577,184 B2
(45) Date of Patent: Mar. 17, 2026

(54) PRODUCTION OF 2,2,4,4-TETRAMETHYL-CYCLOBUTANE-1,3-DIOL FROM ISOBUTANOL USING A HOMOGENEOUS CATALYST

(71) Applicant: Eastman Chemical Company, Kingsport, TN (US)

(72) Inventors: Mesfin Ejerssa Janka, Kingsport, TN (US); Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 421 days.

(21) Appl. No.: 18/250,587

(22) PCT Filed: Nov. 30, 2021

(86) PCT No.: PCT/US2021/061083

§ 371 (c)(1),
(2) Date: Apr. 26, 2023

(87) PCT Pub. No.: WO2022/119792

PCT Pub. Date: Jun. 9, 2022

(65) Prior Publication Data

US 2023/0399278 A1 Dec. 14, 2023

Related U.S. Application Data

(60) Provisional application No. 63/199,051, filed on Dec. 4, 2020.

(51) Int. Cl.

| | |
|---|---|
| ***C07C 29/145*** | (2006.01) |
| ***B01J 31/20*** | (2006.01) |
| ***B01J 31/22*** | (2006.01) |

(52) U.S. Cl.

CPC ............ *C07C 29/145* (2013.01); *B01J 31/20* (2013.01); *B01J 31/2295* (2013.01);
(Continued)

(58) Field of Classification Search

CPC ... C07C 29/145; C07C 29/143; C07C 45/455; C07C 2601/04; C07C 29/095;
(Continued)

(56) References Cited

U.S. PATENT DOCUMENTS

| | | | |
|---|---|---|---|
| 8,420,868 | B2 | 4/2013 | Liu et al. |
| 9,238,602 | B1 | 1/2016 | Stavinoha, Jr. et al. |

(Continued)

FOREIGN PATENT DOCUMENTS

| | | | |
|---|---|---|---|
| CN | 103694083 | A | 4/2014 |
| CN | 105732329 | B | 10/2018 |

(Continued)

OTHER PUBLICATIONS

Co-pending U.S. Appl. No. 18/250,581, filed Apr. 26, 2023; Janka et al.; now U. S. Publication No. 2023-0406792.

(Continued)

*Primary Examiner* — Deborah D Carr

(74) *Attorney, Agent, or Firm* — Tammye L. Taylor Polk

(57) ABSTRACT

Disclosed is a process for preparing 2,2,4,4-tetramethylcyclobutane-1,3-diol by reacting 2,2,4,4-tetramethylcyclobutane dione with isobutanol in the presence of a tandem transfer hydrogenation and Tischenko reaction catalyst.

20 Claims, 1 Drawing Sheet

(52) U.S. Cl.
CPC .. *B01J 2231/643* (2013.01); *B01J 2531/0208* (2013.01); *B01J 2531/821* (2013.01)

(58) Field of Classification Search
CPC ......... C07C 29/14; C07C 45/64; C07C 51/09; C07C 67/00; B01J 31/20; B01J 31/2295; B01J 2231/643; B01J 2531/0208; B01J 2531/821
See application file for complete search history.

(56) References Cited

U.S. PATENT DOCUMENTS

| | | | | |
|---|---|---|---|---|
| 9,238,603 | B1 | 1/2016 | Stavinoha, Jr. et al. | |
| 9,533,928 | B2 | 1/2017 | Dong et al. | |
| 9,988,329 | B1 | 6/2018 | Janka et al. | |
| 10,099,978 | B2 | 10/2018 | Chan et al. | |
| 2008/0132738 | A1 | 6/2008 | McCusker-Orth et al. | |
| 2012/0149946 | A1 * | 6/2012 | Liu | C07C 29/145 568/839 |
| 2017/0334815 | A1 * | 11/2017 | Chan | B01J 37/06 |

FOREIGN PATENT DOCUMENTS

| | | | |
|---|---|---|---|
| CN | 110124674 | A | 8/2019 |
| CN | 111423307 | A | 7/2020 |
| CN | 111875487 | A | 11/2020 |
| CN | 112047834 | A | 12/2020 |
| CN | 110105186 | B | 4/2022 |
| CN | 111905755 | B | 7/2022 |
| CN | 112023919 | B | 7/2022 |
| CN | 112023939 | B | 7/2022 |
| CN | 110170280 | | 9/2022 |
| CN | 112047813 | B | 12/2022 |
| CN | 112174797 | B | 12/2022 |
| CN | 112079700 | B | 3/2023 |
| WO | WO 2018 148092 | A1 | 8/2018 |

OTHER PUBLICATIONS

Non-Final Office Communication received in U.S. Appl. No. 18/250,581 dated Sep. 8, 2025.

Notification of Transmittal of the International Search Report and the Written Opinion of the International Searching Authority, or the Declaration date of mailing Mar. 9, 2022 received in International Application No. PCT/US2021/061083.

Notification of Transmittal of the International Search Report and the Written Opinion of the International Searching Authority, or the Declaration date of mailing Mar. 9, 2022 received in International Application No. PCT/US2021/061085.

Madeleine C. Warner, Charles P. Casey, Jan E. Bäckvall "Shvo's Catalyst in Hydrogen Transfer Reactions" Top. Organomet. Chem. 37, pp. 85-125 (2011).

Menashe, Naim and Shvo, Youval; "Catalytic Disproportionation of Aldehydes with Ruthenium Complexes"; Organometallics, vol. 10, 1991, pp. 3885-3891.

Yigal Blum and Youval Shvo "Catalytically Reactive Ruthenium Intermediates in the Homogeneous Oxidation of Alcohols to Esters." Isr. J. Chem. 24, pp. 144-148 (1984).

Yigal Blum, Youval Shvo and Daniel F. Chodosh "Structure of (?4-Ph4C5CO)(CO)3Ru—a Catalyst Precursor in Hydrogen Transfer and Dehydrogenation Reactions of Alcohols" Inorg. Chim Acta 97, pp. L25-L26 (1985).

* cited by examiner

PRODUCTION OF 2,2,4,4-TETRAMETHYLCYCLOBUTANE-1,3-DIOL FROM ISOBUTANOL USING A HOMOGENEOUS CATALYST

CROSS-REFERENCE TO RELATED APPLICATION(S)

This application is a national stage filing under 35 USC § 371 of International Application Number PCT/US2021/061083, filed on Nov. 30, 2021 which claims the benefit of the filing date to U.S. Provisional Application No. 63/199,051, filed on Dec. 4, 2020, the entire disclosures of which are incorporated by reference herein.

FIELD OF THE INVENTION

This disclosure generally relates to a homogeneous catalytic process for preparing 2,2,4,4-tetramethylcyclobutane-1,3-diol by reacting 2,2,4,4-tetramethylcyclobutanedione with isobutanol.

BACKGROUND OF THE INVENTION

Conventionally, 2,2,4,4-tetramethylcyclobutane-1,3-diol (TMCD) can be produced by the hydrogenation of 2,2,4,4-tetramethylcyclobutanedione (dione) using a ruthenium-containing mixed-metal heterogeneous catalyst.

In this conventional process, TMCD can be produced by (i) conversion of isobutyric acid to isobutyric anhydride, (ii) converting isobutyric anhydride to dione, and (iii) hydrogenation of dione to TMCD.

In this conventional process hydrogen is required. This process operates at relatively high pressure of hydrogen and suffers from the production of a number of byproducts, some produced by acid-catalyzed cyclobutane ring-opening during the hydrogenation process.

In the present disclosure a new process is disclosed that converts 2,2,4,4-tetramethylcyclobutanedione to 2,2,4,4-tetramethylcyclobutane-1,3-diol using isobutanol in place of hydrogen with the coproduction of isobutyl isobutyrate (IBIB). This new process is hydrogen free and eliminates the safety concerns associated with the use of hydrogen. This new process is a highly efficient method for the single-step production of both TMCD and IBIB. Hydrogen transfer from isobutanol to dione replaces the $H_2$-dependent reduction of dione to diol while at the same time isobutanol is converted to IBIB.

The present disclosure addresses these unmet needs as well as others, which will become apparent from the following description and the appended claims.

SUMMARY OF THE INVENTION

The process of the present disclosure is as set forth in the appended claims.

One embodiment of the present disclosure is a process for producing 2,2,4,4-tetramethylcyclobutane-1,3-diol which comprises: (1) contacting 2,2,4,4-tetramethylcyclobutanedione with isobutanol in the presence of a tandem transfer hydrogenation and Tischenko reaction catalyst to produce isobutyl isobutyrate and 2,2,4,4-tetramethylcyclobutane-1,3-diol and 3-hydroxy-2,2,4,4-tetramethylcyclobutanone; (2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol; (3) hydrolyzing the isobutyl isobutyrate optionally in the presence of an acid catalyst to produce isobutyric acid and isobutanol, and optionally wherein the isobutanol is recycled to step (1); (4) converting the isobutyric acid to 2,2,4,4-tetramethylcyclobutanedione wherein the 2,2,4,4-tetramethylcyclobutanedione is optionally recycled to step (1).

One embodiment of the present disclosure is a process for producing 2,2,4,4-tetramethylcyclobutane-1,3-diol which comprises: (1) contacting 2,2,4,4-tetramethylcyclobutanedione with isobutanol in the presence of a tandem ruthenium transfer hydrogenation and Tischenko reaction catalyst comprising one or more of $H_2Ru(PPh_3)_4$, $Ru_3(CO)_{12}$, $(Ar_4C_4CO)Ru(CO)_3$ and $(Ar_4C_4CO)_2H(\mu\text{-}H)(CO)_4Ru_2$, to produce isobutyl isobutyrate and 2,2,4,4-tetramethylcyclobutane-1,3-diol and 3-hydroxy-2,2,4,4-tetramethylcyclobutanone, wherein $(Ar_4C_4CO)Ru(CP)_3$ is represented by the general formula:

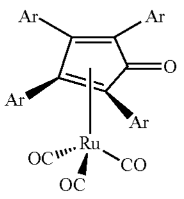

and Ar is represented by the general formula:

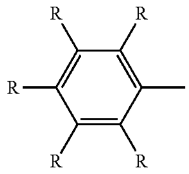

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

and wherein $(Ar_4C_4CO)_2H(\mu\text{-}H)(CO)_4Ru_2$ is represented by the general formula:

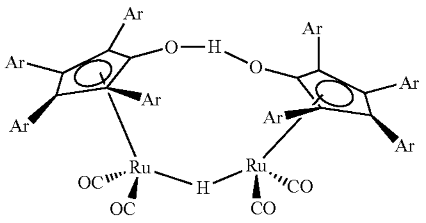

and Ar is represented by the general formula:

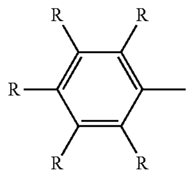

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl.

(2) optionally hydrogenating any un reacted 2,2,4,4-tetramethylcyclobutanedione and 3-hydroxy-2,2,4,4-tetramethylcyclobutanone to produce 2,2,4,4-tetramethylcyclobutane-1,3-diol (3) hydrolyzing the isobutyl isobutyrate optionally in the presence of an acid catalyst to produce isobutyric acid and isobutanol, and optionally wherein the isobutanol is optionally recycled to step (1);

(4) converting the isobutyric acid to 2,2,4,4-tetramethylcyclobutanedione, wherein the 2,2,4,4-tetramethylcyclobutanedione is optionally recycled to step (1).

One embodiment of the present disclosure is a process for producing 2,2,4,4-tetramethylcyclobutane-1,3-diol which comprises: A process for the producing 2,2,4,4-tetramethylcyclobutane-1,3-diol comprising: (1) contacting 2,2,4,4-tetramethylcyclobutanedione with isobutanol in the presence of a tandem ruthenium transfer hydrogenation and Tischenko reaction catalyst selected from (($Ph_4C_4CO)_2H(\mu$-H)$(CO)_4Ru_2$). $(Ph_4C_4CO)_2H(\mu$-H)$(CO)_4Ru_2$, [$(4-ClC_6H_4)_4C_4CO_2$]H($\mu$-H)$(CO)_4Ru_2$, [2,5-$(C_6H_5)_2$-3,4-$(4-MeOC_6H_4)_2C_4CO]_2H(\mu$-H)$(CO)_4Ru_2$, or [2,5-$(C_6H_5)_2$-3,4-$(4-FC_6H_4)_2C_4CO]_2H(\mu$-H)$(CO)_4Ru_2$ to produce isobutyl isobutyrate and 2,2,4,4-tetramethylcyclobutane-1,3-diol and 3-hydroxy-2,2,4,4-tetramethylcyclobutanone; (2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol; (3) hydrolyzing the isobutyl isobutyrate optionally in the presence of an acid catalyst to produce isobutyric acid and isobutanol, and optionally wherein the isobutanol is optionally recycled to step (1); (4) converting the isobutyric acid to 2,2,4,4-tetramethylcyclobutanedione. wherein the 2,2,4,4-tetramethylcyclobutanedione is optionally recycled to step (1).

One embodiment of the present disclosure is a process for producing 2,2,4,4-tetramethylcyclobutane-1,3-diol which comprises:

(1) contacting 2,2,4,4-tetramethylcyclobutanedione with isobutanol in the presence of a tandem transfer hydrogenation and Tischenko reaction catalyst to produce isobutyl isobutyrate and 2,2,4,4-tetramethylcyclobutane-1,3-diol and 3-hydroxy-2,2,4,4-tetramethylcyclobutane;

(2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol (3) hydrolyzing the isobutyl isobutyrate optionally in the presence of an acid catalyst to produce isobutyric acid and isobutanol, and wherein the isobutanol is optionally recycled to step (1);

(4) converting the isobutyric acid to 2,2,4,4-tetramethylcyclobutanedione, wherein the 2,2,4,4-tetramethylcyclobutanedione is optionally recycled to step (1).

One embodiment of the present disclosure is a process for producing 2,2,4,4-tetramethylcyclobutane-1,3-diol which comprises:

1. contacting 2,2,4,4-tetramethylcyclobutanedione with isobutanol in the presence of a tandem ruthenium transfer hydrogenation and Tischenko reaction catalyst comprising one or more of $H_2Ru(PPh_3)_4$, $Ru_3(CO)_{12}$, $(Ar_4C_4CO)Ru(CO)_3$ and $(Ar_4C_4CO)_2H(\mu$-H)$(CO)_4Ru_2$, to produce isobutyl isobutyrate and 2,2,4,4-tetramethylcyclobutane-1,3-diol and 3-hydroxy-2,2,4,4-tetramethylcyclobutanone, wherein $(Ar_4C_4CO)Ru(CO)_3$ is represented by the general formula:

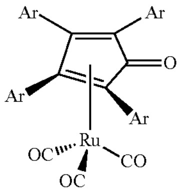

and Ar is represented by the general formula:

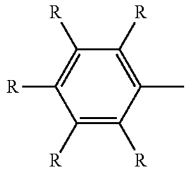

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

and wherein $(Ar_4C_4CO)_2H(\mu$-H)$(CO)_4Ru_2$ is represented by the general formula:

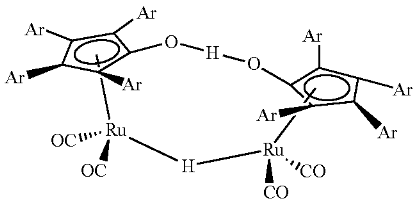

and Ar is represented by the general formula:

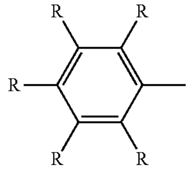

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

2. optionally hydrogenating any un reacted 2,2,4,4-tetramethylcyclobutanedione and 3-hydroxy-2,2,4,4-tetramethylcyclobutanone to produce 2,2,4,4-tetramethylcyclobutane-1,3-diol
3. hydrolyzing the isobutyl isobutyrate optionally in the presence of an acid catalyst to produce isobutyric acid and isobutanol, and optionally wherein the isobutanol is optionally recycled to step (1);
4. converting the isobutyric acid to 2,2,4,4-tetramethylcyclobutanedione, wherein the 2,2,4,4-tetramethylcyclobutanedione is optionally recycled to step (1). One embodiment of the present disclosure is a process for the producing 2,2,4,4-tetramethylcyclobutane-1,3-diol which comprises:

1. contacting 2,2,4,4-tetramethylcyclobutanedione with isobutanol in the presence of a tandem ruthenium transfer hydrogenation and Tischenko reaction catalyst selected from $(Ph_4C_4CO)_2H(\mu\text{-}H)(CO)_4Ru_2$, $[(4\text{-}ClC_6H_4)_4C_4CO]_2H(\mu\text{-}H)(CO)_4Ru_2$, $[2,5\text{-}(C_6H_5)_2\text{-}3,4\text{-}(4\text{-}MeOC_6H_4)_2C_4CO]_2H(\mu\text{-}H)(CO)_4Ru_2$, or $[2,5\text{-}(C_6H_5)_2\text{-}3,4\text{-}(4\text{-}FC_6H_4)_2C_4CO]_2H(\mu\text{-}H)(CO)_4Ru_2$ to produce isobutyl isobutyrate and 2,2,4,4-tetramethylcyclobutane-1,3-did and 3-hydroxy-2,2,4,4-tetramethylcyclobutanone;
2. optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol
3. hydrolyzing the isobutyl isobutyrate optionally in the presence of an acid catalyst to produce isobutyric acid and isobutanol, and wherein the isobutanol is optionally recycled to step (1);
4. converting the isobutyric acid to 2,2,4,4-tetramethylcyclobutane-dione, wherein the 2,2,4,4-tetramethylcyclobutanedione is optionally recycled to step (1).

In one embodiment of the present disclosure the tandem ruthenium transfer hydrogenation and Tischenko reaction catalyst is $((Ph_4C_4CO)_2H(\mu\text{-}H)(CO)_4Ru_2)$.

In one embodiment of the present disclosure, the conversion of the 2,2,4,4-tetramethylcyclobutanedione is at least 50% or at least 70% or at least 90%.

In one embodiment of the present disclosure, the selectivity of 2,2,4,4-tetramethylcyclobutane-1,3-diol is at least 30%, or at least 60%.

DETAILED DESCRIPTION OF THE INVENTION

Figure 1:
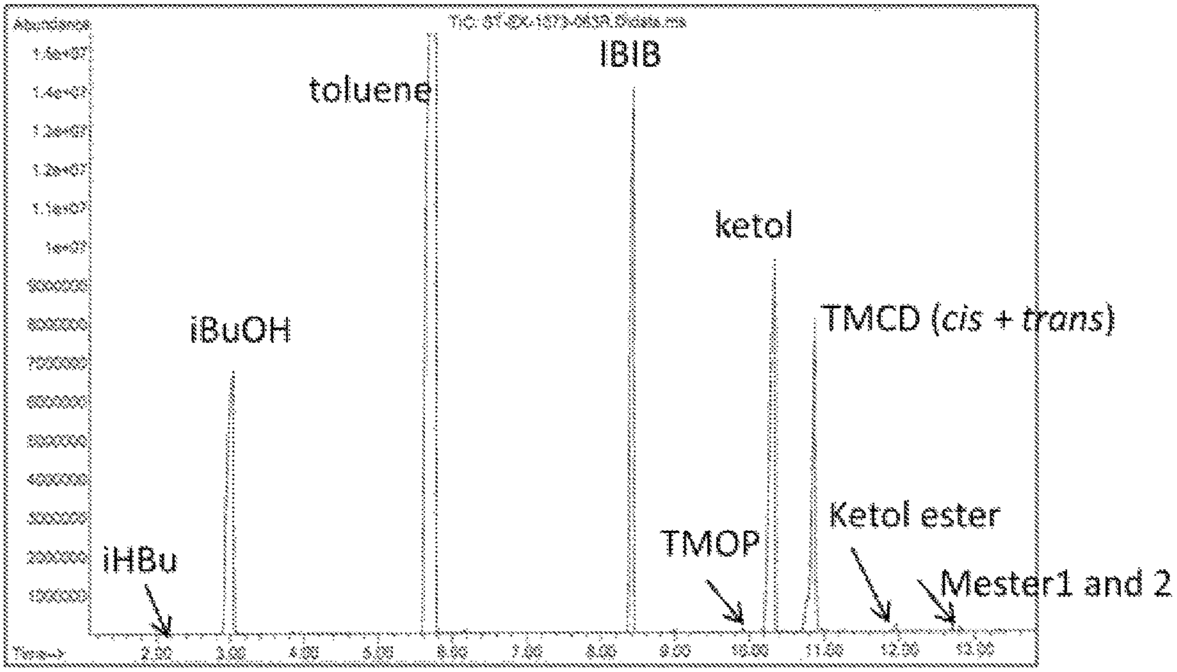
FIG. 1 is a GC/MS chromatogram of a reaction product. 4:1 mole ratio of iBuOH to dione was used. (1-hydroxy-2,2,4-trimethylpentan-3-one (TMOP), 3-hydroxy-2,2,4,4-tetramethylcyclobutyl isobutyrate (Mester1/2). See example 1 in the experimental section.

In the present disclosure, it has been discovered that in a single process step TMCD can be formed from a dione and isobutanol. The isobutanol-to-TMCD process of the present disclosure also converts isobutyric acid to isobutyric anhydride (IBAN) and IBAN to dione.

This process enables the single-step production of both TMCD and isobutyl isobutyrate (IBIB). Hydrogen transfer from isobutanol to dione replaces the $H_2$-dependent reduction of dione to diol while at the same time isobutanol is oxidized to the carboxylic acid level as needed for its conversion to dimethyl ketene. The efficiency of the mild dehydrogenative coupling of isobutanol to IBIB, followed by acid-catalyzed hydrolysis to isobutyric acid, provides a higher yield of isobutyric acid relative to the air-oxidation of isobutyraldehyde which suffers from the coproduction of isopropyl formate (and the associated isopropanol and formic acid).

The present disclosure is for a single process step in which 2,2,4,4-tetramethylcyclobutane-1,3-diol (TMCD) is formed from 2,2,4,4-tetramethylcyclobutanedione (dione) and isobutanol. The dione and the isobutanol is oxidized to the acid oxidation state under mild conditions with essentially quantitative yield. During the process of the present disclosure, the IBIB is hydrolyzed in a separate step due to the need for acid catalysis of this hydrolysis and the acid sensitivity of TMCD product.

In one embodiment, the present disclosure provides a process for preparing 2,2,4,4-tetramethylcyclobutane-1,3-diol. The process comprises contacting 2,2,4,4-tetramethylcyclobutanedione with isobutanol in the presence of a tandem transfer hydrogenation and Tischenko reaction catalyst.

One embodiment of this disclosure is a process which utilizes isobutanol as the raw material for production of TMCD. In some embodiments, bio-isobutanol may be used as the Isobutanol source in this disclosure, thus producing a bio-TMCD. If an isobutanol with partial bio-content is employed, then a bio-TMCD with a corresponding partial bio-content is produced. Likewise, where bio-isobutanol with 25-100% bio-content is employed in the four-step process shown below, then intermediates such as bio-IBIB, bio-isobutyric acid, and bio-IBAN may also be produced. In applications where bio-TMCD with 25-100% bio-content is introduced into a copolyester, a novel polyester with appropriate bio-content may be produced. Compositions of bio-TMCD from 25-100% are anticipated by this process as derived from the corresponding bio-IBIB of the first step, the bio-isobutyric acid of step two and the bio-IBAN of step three. In one embodiment of the present disclosure, the isobutanol comprises at least 25% bio-isobutanol. In one embodiment of the present disclosure, the isobutanol comprises at least 50% bio-isobutanol. In one embodiment of the present disclosure, the isobutanol comprises at least 75% bio-isobutanol. In one embodiment of the present disclosure, the isobutanol comprises 100% bio-isobutanol.

In one embodiment of the present disclosure, the process requires the following:

(i) the transfer-hydrogenation of tetramethylcyclobutane dione using isobutanol as the hydrogen donor with the co-production of IBIB, (ii) the hydrolysis of IBIB yielding isobutyric acid and isobutanol (in some embodiments, the isobutanol produced is recycled to step (i)), (iii) production of isobutyric anhydride using isobutyric acid (in some embodiments, the isobutyric acid is generated in step (ii)), and (iv) production of dimethylketene by converting the isobutyric anhydride.

In one embodiment of the present disclosure, the process is as follows:

(i)

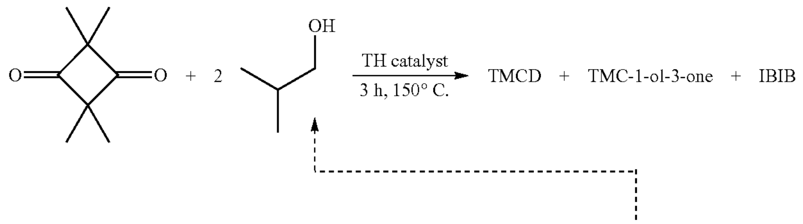

(ii)

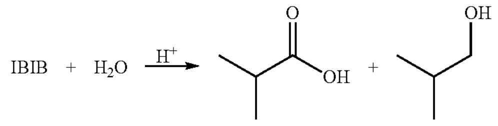

(iii)

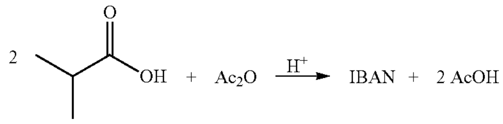

(iv)

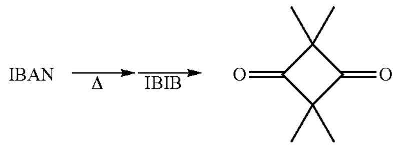

In one embodiment, the isobutanol-to-TMCD process of this disclosure requires the conversion isobutyric acid to IBAN and IBAN to dione. Hydrogen transfer from isobutanol to dione replaces the $H_2$-dependent reduction of dione to diol while at the same time isobutanol is oxidized to the carboxylic acid level as needed for its conversion to dimethyl ketene. The efficiency of the mild dehydrogenative coupling of isobutanol to IBIB provides higher yield of isobutyric acid and does not suffer from the coproduction of isopropyl formate (or the associated isopropanol).

In one embodiment, the process of the present disclosure comprises contacting 2,2,4,4-tetramethylcyclobutanedione with isobutanol in the presence of a tandem transfer hydrogenation and Tischenko reaction catalyst to produce isobutyl isobutyrate and 2,2,4,4-tetramethylcyclohutane-1,3-diol and 3-hydroxy-2,2,4,4-tetramethylcyclobutanone.

Thus, the present disclosure provides a process for preparing 2,2,4,4-tetramethylcyclobutane-1,3-diol by reacting 2,2,4,4-tetramethylcyclobutanedione with isobutanol in the presence of a tandem transfer hydrogenation and Tischenko reaction catalyst.

One embodiment of the present disclosure is a process for producing 2,2,4,4-tetramethylcyclobutane-1,3-diol which comprises:

1) contacting 2,2,4,4-tetramethylcyclobutanedione with isobutanol in the presence of a tandem ruthenium transfer hydrogenation and Tischenko reaction catalyst comprising one or more of $H_2Ru(PPh_3)_4$, $Ru_3(CO)_{12}$, $(Ar_4C_4CO)Ru(CO)_3$ and $(Ar_4C_4CO)_2H(\mu\text{-}H)(CO)_4Ru_2$, to produce isobutyl isobutyrate and 2,2,4,4-tetramethylcyclobutane-1,3-diol and 3-hydroxy-2,2,4,4-tetramethylcyclobutanone, wherein $(Ar_4C_4CO)Ru(CO)_3$ is represented by the general formula:

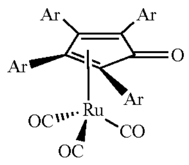

and Ar is represented by the general formula:

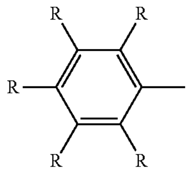

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

and wherein $(Ar_4C_4CO)_2H(\mu\text{-}H)(CO)_4Ru_2$ is represented by the general formula:

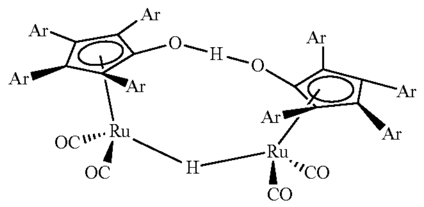

and Ar is represented by the general formula:

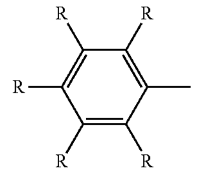

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol 3) hydrolyzing the isobutyl isobutyrate optionally in the presence of an acid catalyst to produce isobutyric acid and isobutanol, and optionally wherein the isobutanol is optionally recycled to step 1).

4) converting the isobutyric acid to 2,2,4,4-tetramethylcyclobutanedione, wherein the 2,2,4,4-tetramethylcyclobutanedione is optionally recycled to step (1).

One embodiment of the present disclosure is a process for the producing 2,2,4,4-tetramethylcyclobutane-1,3-diol which comprises:

1) contacting 2,2,4,4-tetramethylcyclobutanedione with isobutanol in the presence of a tandem ruthenium transfer hydrogenation and Tischenko reaction catalyst selected from (Ph4C4CO)2H(μ-H)(CO)4Ru2, $[(4\text{-}ClC_6H_4)_4C_4CO]_2H(\mu\text{-}H)(CO)_4Ru_2$, $[2,5\text{-}(C_6H_5)_2\text{-}3,4\text{-}(4\text{-}MeOC_6H_4)_2C_4CO]_2H(\mu\text{-}H)(CO)_4Ru_2$, or $[2,5\text{-}(C_6H_4)_2\text{-}3,4\text{-}(4\text{-}FC_6H_4)_2C_4CO]_2H(\mu\text{-}H)(CO)_4Ru_2$ to produce isobutyl isobutyrate and 2,2,4,4-tetramethylcyclobutane-1,3-diol and 3-hydroxy-2,2,4,4-tetramethyloyclobutanone;

2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol 3) hydrolyzing the isobutyl isobutyrate optionally in the presence of an acid catalyst to produce isobutyric acid and isobutanol, and wherein the isobutanol is optionally recycled to step 1)

4) converting the isobutyric acid to 2,2,4,4-tetramethylcyclobutanedione, wherein the 2,2,4,4-tetramethylcyclobutanedione is optionally recycled to step (1).

In one embodiment, the process of the present disclosure comprises contacting a dione with an alcohol at a alcohol-to-dione molar ratio of greater than 1:1 and up to 50:1 in the presence of a tandem transfer hydrogenation and Tischenko reaction catalyst at conditions effective to produce the diol.

In one embodiment, the process of the present disclosure is performed with a isobutanol to 2,2,4,4-tetramethylcyclobutanedione molar ratio of greater than 1:1 and up to 50:1.

In one embodiment, an excess of the alcohol or isobutanol is used to maximize selectivity and to minimize formation of by-products. In some embodiment, the isobutanol to 2,2,4,4-tetramethylcyclobutanedione molar ratios include 1:1 to 50:1, 2:1 to 25:1, 3:1 to 25:1, 4:1 to 25:1, 8:1 to 25:1, 12:1 to 25:1, 16:1 to 25:1, 2:1 to 24:1, 3:1 to 24:1, 4:1 to 24:1, 8:1 to 24:1, 12:1 to 24:1, 16:1 to 24:1, 2:1 to 20:1, 3:1 to 20:1, 4:1 to 20:1, 8:1 to 20:1, 12:1 to 20:1, 16:1 to 20:1, 2:1 to 16:1, 3:1 to 16:1, 4:1 to 16:1, 8:1 to 16:1, and 12:1 to 16:1.

In one embodiment, the tandem ruthenium transfer hydrogenation and Tischenko reaction catalyst is $(Ph_4C_4CO)_2H(\mu\text{—}H)(CO)_4Ru_2$. It is known in the literature as Shvo's catalyst and is sometimes written as $[Ru_2(CO)_4(\mu\text{-}H)(C_4Ph_4COHOCC_4Ph_4)]$. Shvo's catalyst is a cyclopentadienone-ligated diruthenium complex having the structure 1:

1

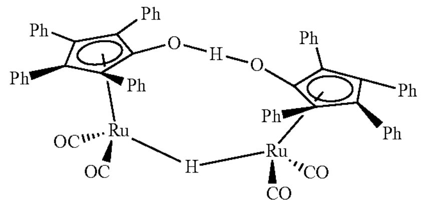

By "ruthenium complex compound" or "RuCC," it is meant a complex compound containing one or more ruthenium atoms and one or more ligands linked by direct metal-ligand bonding. The formal oxidation number of the ruthenium atom, and the type and quantity of groups serving as the ligand are not particularly limiting. Examples of such ligands include carbon monoxide, phosphines, hydrides, and substituted cyclopentadienones. Substituted cyclopentadienones are preferred ligands.

In one embodiment, examples of suitable RuCCs include $H_2Ru(PPh_3)_4$, $Ru_3(CO)_{12}$, (Ar4C4CO)Ru(CO)3 and (Ar4C4CO)2H(μ-H)(CO)$_4$Ru$_2$, $(Ph_4C_4CO)Ru(CO)_3$, $[(4\text{-}ClC_6H_4)_4C_4CO]Ru(CO)_3$, $[2,5\text{-}(C_6H_4)_2\text{-}3,4\text{-}(4\text{-}MeOC_6H_4)_2C_4CO]Ru(CO)_3$, $[2,5\text{-}(C_6H_4)_2\text{-}3,4\text{-}(4\text{-}FC_6H_4)_2C_4C0]Ru(CO)_3$, $(Ph_4C_4CO)_2H(\mu\text{-}H)(CO)_4Ru_2$, $[(4\text{-}ClC_6H_4)_4C_4CO]_2H(\mu\text{-}H)(CO)_4Ru_2$, $[2,5\text{-}(C_6H_5)_2\text{-}3,4\text{-}(4\text{-}MeOC_6H_4)_2C_4CO]_2H(\mu\text{-}H)(CO)_4Ru_2$, and $[2,5\text{-}(C_6H_5)_2\text{-}3,4\text{-}(4\text{-}FC_6H_4)_2C_4CO]_2H(\mu\text{-}H)(CO)_4Ru_2$. These compounds can be synthesized using well-known methods (e.g., N. Menashe et al., *Organometallics*, Vol. 10, p. 3885 (1991)).

In one embodiment, the $(Ar_4C_4CO)Ru(CO)_3$ is represented by the general formula:

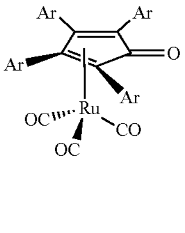

and Ar is represented by the general formula:

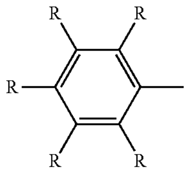

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl;

In one embodiment, $(Ar_4C_4CO)_2H(\mu\text{-}H)(CO)_4Ru_2$ is represented by the general formula:

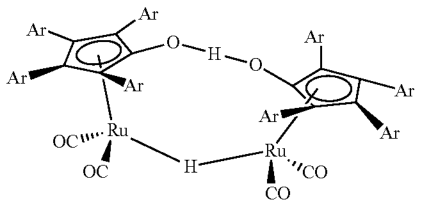

and Ar is represented by the general formula:

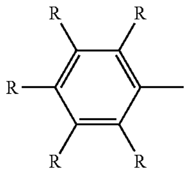

and the groups R are the same or different and are selected from H, methyl, ethyl, or a linear or branched alkyl group containing from 3 to 10 carbon atoms, substituted or unsubstituted aromatic group, a carbonyl-containing group such as aldehyde, ketone or ester with 2-10 carbon atoms, trifluoromethyl or fluorinated hydrocarbon group such as perfluorobutyl or pentaflurophenyl.

In one embodiment, the amount of catalyst used can range from $10^{-7}$ to 1:1 (molar ratio) with respect to the dione. In one embodiment, the amount of catalyst used can range from $10^{-3}$:1 to 0.01:1 (molar ratio) with respect to the dione. In one embodiment, the catalyst concentration is from about 0.001 mole percent to 10 mol percent based on the concentration of the 2,2,4,4-tetramethylcyclobutanedione. In one embodiment, the catalyst concentration, based on the concentration of the 2,2,4,4-tetramethylcyclobutanedione, is from about 0.001 mole percent to about 9 mol percent, or is from about 0.001 mole percent to about 5 mol percent, or is from about 0.001 mole percent to about 1 mol percent, or is from about 0.01 mole percent to about 10 mol percent or is from about 0.01 mole percent to about 5 mol percent, or is from about 0.01 mole percent to about 1 mol percent, or is from about 0.1 mole percent to about 10 mol percent, or is from about 0.1 mole percent to about 5 mol percent, or is from about 0.1 mole percent to about 1 mol percent.

After the reaction, the catalyst can be separated from the products by distillation, extraction, adsorption, or other ordinary methods, and reused. The process of the present disclosure can be carried out without a solvent. But if the RuCC has low solubility in the reaction medium comprising the dione and the alcohol, the reaction can be carried out in a suitable solvent in order to dissolve the RuCC, or as otherwise needed. Examples of suitable solvents include hydrocarbons such as hexane, benzene, and toluene; ethers such as diethyl ether, dimethoxyethane, tetrahydrofuran, and dioxanes; and esters such as ethyl acetate, butyl acetate, and 2-ethylhexyl acetate.

The reaction is typically carried out by introducing the dione, the isobutanol, and the catalyst into a vessel, and then mixing the contents. In one embodiment, the reaction is carried out by introducing the 2,2,4,4-tetramethylcyclobutanedione, the isobutanol, and a tandem transfer hydrogenation and Tischenko reaction catalyst into a vessel, and then mixing the contents. In one embodiment, the reaction temperature can range from 50 to 300° C., or from 50 to 200° C., or from 60 to 200° C., or from 70 to 200° C., or from 80 to 200° C., or from 90 to 200° C., or from 100 to 200° C., or from 150 to 200° C., or from 50 to 150° C., or from 100 to 150° C., or from 50 to 100° C. In one embodiment, the process temperature ranges from about 50° C. to about 300° C. In one embodiment, the process temperature ranges from about 50° C. to about 200° C.

The reaction pressure and atmosphere are not particularly limiting. The reaction may be carried out at less than atmospheric pressure, at atmospheric pressure, or at elevated pressure. In one embodiment, the reaction is carried out in an inert atmosphere, such as nitrogen or argon. In one embodiment, the reaction is carried out in an inert atmosphere, such as nitrogen or argon. In one embodiment, the reaction is carried out under nitrogen pressure to the keep the alcohol in a liquid state. In one embodiment, the reaction is carried out under at least 200 psig of nitrogen pressure.

In one embodiment, the reaction time depends on the reaction temperature and catalyst concentration, and the reaction time can range, for example, from 0.1 to 10 hours, or from 0.5 to 3 hours, or from 5 minutes to 5 hours, or from 5 minutes to 4 hours, or from 5 minutes to 3 hours, or from 5 minutes to 2 hours, or from 5 minutes to 1 hour, or from 5 minutes to 30 minutes, or from 30 minutes to 5 hours, or from 30 minutes to 4 hours, or from 30 minutes to 2 hours, or from 30 minutes to 1 hour.

In one embodiment of the process of the present disclosure is carried at an isobutanol to dione molar ratio of greater than 1:1 and up to 50:1 in the presence of a tandem transfer hydrogenation and Tischenko reaction catalyst at conditions effective to produce isobutyl isobutyrate and 2,2,4,4-tetramethylcyclobutane-1,3-diol and 3-hydroxy-2,2,4,4-tetramethylcyclobutanone. In one embodiment, the concentration of the isobutanol to 2,2,4,4-tetramethylcyclobutanedione is from a mole ratio of 1:1 to 50:1. In one embodiment, the concentration of the isobutanol to 2,2,4,4-tetramethylcyclobutanedione is from a mole ratio of 1:1 to 40:1. In one embodiment, the concentration of the isobutanol to 2,2,4,4-tetramethylcyclobutanedione is from a mole ratio of 1:1 to 30:1.

In one embodiment, the concentration of the isobutanol to 2,2,4,4-tetramethylcyclobutanedione is from a mole ratio of 1:1 to 20:1.

In one embodiment, the concentration of the isobutanol to 2,2,4,4-tetramethylcyclobutanedione is from a mole ratio of 1:1 to 10:1. In one embodiment, the concentration of the isobutanol to 2,2,4,4-tetramethylcyclobutanedione is from a mole ratio of 1:1 to 5:1. In one embodiment, the concentration of the isobutanol to 2,2,4,4-tetramethylcyclobutanedione is from a mole ratio of 1:1 to 2.5:1.

In one embodiment, the process of the disclosure is capable of converting the 2,2,4,4-tetramethylcyclobutanedione at a degree of conversion of at least 50%; or at least 55%, or at least 60%, or at least 65%, or at least 70%, or at least 75%, or at least 80%, or at least 85%, or at least 90%, or at least 95%. In one embodiment, the conversion of the 2,2,4,4-tetramethylcyclobutanedione is at least 70%. In one embodiment, the conversion of the 2,2,4,4-tetramethylcyclobutanedione is at least 80%. In one embodiment, the conversion of the 2,2,4,4-tetramethylcyclobutanedione is at least 90%.

In some embodiments, the degree of conversion is determined by the following equation:

$$\%\ \text{Conversion} = \frac{\text{moles of dione consumed}}{\text{moles of dione fed}} \times 100$$

In some embodiments, the process of the present disclosure can have selectivity of 2,2,4,4-tetramethylcyclobutane-1,3-diol of at least 30%, or at least 40%, or at least 50%, or at least 60%, or at least 70%, or at least 80% or at least 90% or at least 95%. In one embodiment, the selectivity of 2,2,4,4-tetramethylcyclobutane-1,3-diol is at least 30%. In one embodiment, the selectivity of 2,2,4,4-tetramethylcyclobutane-1,3-diol is at least 50%. In one embodiment, the selectivity of 2,2,4,4-tetramethylcyclobutane-1,3-diol is at least 60%.

The present disclosure includes and expressly contemplates any and all combinations of embodiments, features, characteristics, parameters, and/or ranges disclosed herein. That is, the present disclosure may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

While attempts have been made to be precise, the numerical values and ranges described herein should be considered to be approximations (even when not qualified by the term "about"). These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This disclosure can be further illustrated by the following examples of preferred embodiments thereof, although it will be understood that these examples are included merely for purposes of illustration and are not intended to limit the scope of the disclosure.

EXAMPLES

A tandem TH-Tishchenko reaction of i-BuOH and dione was conducted using Shvo's catalyst 1. The experiment was performed at 150° C. for 3 h using 0.1 mol % catalyst (with respect to dione). After 3 h of reaction, the reaction product was analyzed using Gas Chromatography-Mass Spectrometry (GC-MS). The chromatogram (FIG. 1) shows the reaction proceeded cleanly to make IBIB and a mixture of ketol and TMCD products (eq 1).

(V)

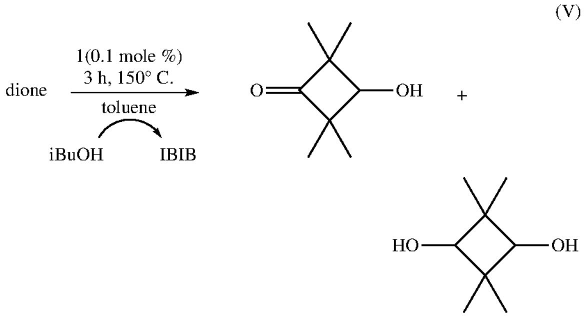

Figure 2:
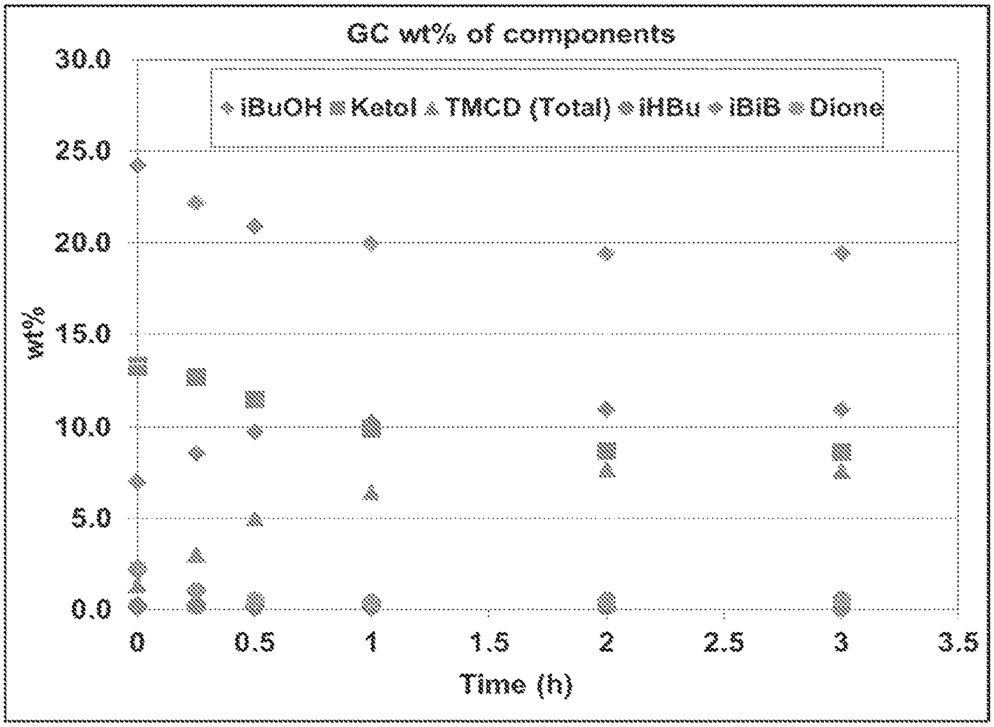
FIG. 2 is a reaction kinetic studies.

A kinetic study was conducted at 150° C. using 4:1 mole ratio of iBuOH and dione feeds and 0.1 mol % of Shvo's catalyst. The reaction reached equilibrium in about 2 h (FIG. 2). Most of the dione was consumed in less than 2 h. The combined selectivities to Ketol and TMCD products remain very high during the reaction (Table 1). In addition the selectivity to 1131B remained over 96%.

TABLE 1

Tandem TH-Tishchenko reaction of isobutanol and dione.[a]

| Time (hr) | % conversion of dione | % selectivity of ketol[b] | % selectivity of TMCD (cis + trans)[b] | % selectivity of IBIB[b] |
|---|---|---|---|---|
| 0.25 | 93.6% | 80.4% | 19.0% | 98.1% |
| 0.5 | 96.8% | 70.6% | 30.5% | 97.8% |
| 1 | 97.5% | 60.2% | 38.6% | 95.2% |
| 2 | 96.9% | 53.3% | 46.5% | 96.4% |
| 3 | 96.5% | 53.0% | 46.2% | 96.4% |

[a]4:1 mole ratio of iBuOH to dione was used as a feed. 0.1 mol % Shvo's catalyst loading. The experiment was conducted at 150° C. There was a 12 min heat-up time before t = 0 min sample was taken.

[b]Selectivities were calculated as number of moles of the product in the liquid phase divided by the number of mole of reactant charged. Cis/trans ratio of TMCD remained around 1.3 during the reaction (see example 2 in experimental section).

Experimental

Materials: iBuOH and toluene were purchased from Aldrich. Shvo's catalyst was obtained from Strem.

Gas Chromatographic Method. Process samples were analyzed by using an Agilent gas chromatograph Model 6890 equipped with a split/heated injector (250° C.) and a thermo couple detector (250° C.). A capillary column (30 meter×0.32 mm ID) coated with (50% methyl,50% phenyl silicone) at 0.25 μm film thickness (such as DB-Wax or equivalent) was employed. Helium was used as the carrier gas with an initial column head pressure of 7.42 psi and an initial column flow of 1.56 mL/minute while the carrier gas linear velocity of 45 cm/second was maintained constant throughout the entire oven temperature program. The column temperature was programmed as follows: The initial oven temperature was set at 40° C. and was held for 3 minutes, the oven was ramped up to 200° C. at 8° C./minute and was held at 200° C. for 2 minutes (the total run time was 25 mins). 0.5-μl of the prepared sample solution was injected with a split ratio of 75:1. EZ-Chrom Elite chromatography data system software was used for data acquisition and data processing. The sample preparation was done by weighing 0.1 g (accurate to 0.1 mg) of sample in a GC vial and adding 1.0 mL ISTD solution (1% by volume of diethylene glycol dimethyl either in acetonitrile) to the GC vial. The GC components of this method are shown below.

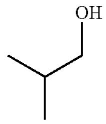

isobutanol
iBuOH

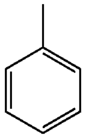

toluene

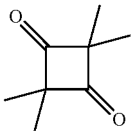

2,2,4,4-tetramethylcyclobutane-1,3-dione
Dione

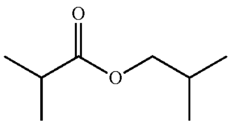

isobutyl isobutyrate
iBiB

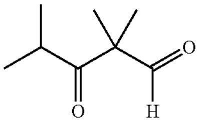

2,2,4-trimethyl-3-oxopentanal
Ketone-Aldehyde

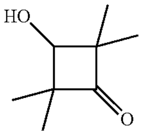

3-hydroxy-2,2,4,4-tetramethyl cyclobutanone
Ketol

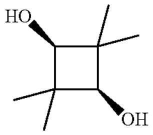

cis-2,2,4,4-tetramethyl cyclobutane-1,3-diol
cis TMCD

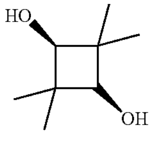

trans-2,2,4,4-tetramethyl cyclobutane-1,3-diol
transTMCD

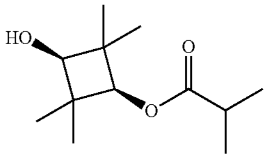

cis-3-hydroxy-2,2,4,4-tetramethyl cyclobutyl isobutyrate
Mester1

-continued

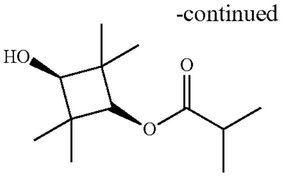

trans-3-hydroxy-2,2,4,4-tetramethyl cyclobutyl isobutyrate
Mester2

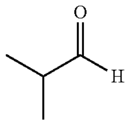

isobutyraldehyde
iHBu

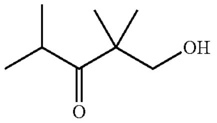

1-hydroxy-2,2,4-trimethyl pentan-3-one
TMOP

Chemical structures of GC components analyzed by the method.

Example 1. A 100 mL titanium autoclave was charged with 20.0 g (269.2 mmol) of iBuOH, 10.7 g (76.3 mmol) of dione and 0.09 g (0.077 mmol) of Shvo catalyst. The autoclave was pressurized with about 100 psig of $N_2$ and 15 then vented two times. Then it was pressurized with 200 psig of $N_2$ again and the closed autoclave was heated to 150° C. and kept at reaction temperature for 3 h. It was then cooled to room temperature and depressurized. The liquid product was analyzed by GC/MS chromatography (FIG. 1).

Example 2. A 100 mL titanium autoclave was charged with 20.0 g (269.2 mmol) of iBuOH, 10.7 g (76.3 mmol) of dione and 0.09 g (0.077 mmol) of Shvo catalyst. The autoclave was pressurized with about 100 psig of $N_2$ and then vented two times. Then it was pressurized with 200 psig of $N_2$ again and the closed autoclave was heated to 150° C. and kept at reaction temperature for 3 h. At t=0 sample was taken and the mass recorded. Samples were taken at t=15 min, 30 min, 60 min, 90 min, 120 min and 180 min. After 3 h the autoclave was cooled to room temperature and depressurized. The samples were analyzed by gas chromatography (FIG. 2). Conversions and selectivities are given in Table 1

This disclosure has been described in detail with particular reference to preferred embodiments thereof, but it will be understood that variations and modifications can be effected within the spirit and scope of the invention.

We claim:

1. A process for producing 2,2,4,4-tetramethylcyclobutane-1,3-diol comprising:

(1) contacting 2,2,4,4-tetramethylcyclobutanedione with isobutanol in the presence of a tandem transfer hydrogenation and Tischenko reaction catalyst to produce isobutyl isobutyrate and 2,2,4,4-tetramethylcyclobutane-1,3-diol and 3-hydroxy-2,2,4,4-tetramethylcyclobutanone;

(2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol;

(3) hydrolyzing the isobutyl isobutyrate optionally in the presence of an acid catalyst to produce isobutyric acid and isobutanol, and optionally wherein the isobutanol is optionally recycled to step (1);

(4) converting the isobutyric acid to 2,2,4,4-tetramethylcyclobutanedione wherein the 2,2,4,4-tetramethylcyclobutanedione is optionally recycled to step (1).

2. A process for producing 2,2,4,4-tetramethylcyclobutane-1,3-diol comprising:

(1) contacting 2,2,4,4-tetramethylcyclobutanedione with isobutanol in the presence of a tandem ruthenium transfer hydrogenation and Tischenko reaction catalyst comprising one or more of $H_2Ru(PPh_3)_4$, $Ru_3(CO)_{12}$, $(Ar_4C_4CO)Ru(CO)_3$, and $(Ar_4C_4CO)_2H(\mu\text{-}H)\ (CO)_4Ru_2$, to produce isobutyl isobutyrate and 2,2,4,4-tetramethylcyclobutane-1,3-diol and 3-hydroxy-2,2,4,4-tetramethylcyclobutanone, wherein $(Ar_4C_4CO)Ru(CO)_3$ is represented by the general formula:

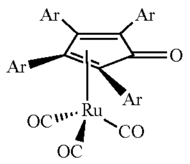

and Ar is represented by the general formula:

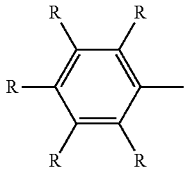

and the groups R are the same or different and are selected from H, methyl, ethyl, or a linear or branched alkyl group containing from 3 to 10 carbon atoms, substituted or unsubstituted aromatic group, an aldehyde, a ketone or an ester with 2-10 carbon atoms, trifluoromethyl or a fluorinated hydrocarbon group;

and wherein $(Ar_4C_4CO)_2H(\mu\text{-}H)(CO)_4Ru_2$ is represented by the general formula:

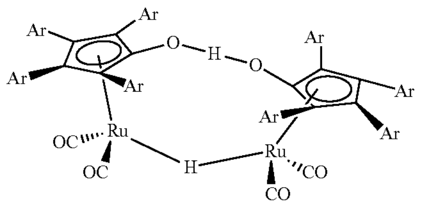

and Ar is represented by the general formula:

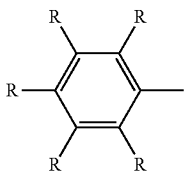

and the groups R are the same or different and are selected from H, methyl, ethyl, or a linear or branched alkyl group containing from 3 to 10 carbon atoms, substituted or unsubstituted aromatic group, an aldehyde, a ketone or an ester with 2-10 carbon atoms, trifluoromethyl or a fluorinated hydrocarbon group;

(2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol;

(3) hydrolyzing the isobutyl isobutyrate optionally in the presence of an acid catalyst to produce isobutyric acid and isobutanol, and optionally wherein the isobutanol is optionally recycled to step (1);

(4) converting the isobutyric acid to 2,2,4,4-tetramethylcyclobutanedione, wherein the 2,2,4,4-tetramethylcyclobutanedione is optionally recycled to step (1).

3. A process for the producing 2,2,4,4-tetramethylcyclobutane-1,3-diol comprising:

(1) contacting 2,2,4,4-tetramethylcyclobutanedione with isobutanol in the presence of a tandem ruthenium transfer hydrogenation and Tischenko reaction catalyst selected from $((Ph_4C_4CO)_2H(\mu\text{-}H)(CO)_4Ru_2)$-$(Ph_4C_4CO)_2H(\mu\text{-}H)(CO)_4Ru_2$, $[(4\text{-}ClC_6H_4)_4C_4CO]_2H(\mu\text{-}H)(CO)_4Ru_2$, $[2,5\text{-}(C_6H_5)_2\text{-}3,4\text{-}(4\text{-}MeOC_6H_4)_2C_4CO]_2H(\mu\text{-}H)(CO)_4Ru_2$, or $[2,5\text{-}(C_6H_5)_2\text{-}3,4\text{-}(4\text{-}FC_6H_4)_2C_4CO]_2H(\mu\text{-}H)(CO)_4Ru_2$ to produce isobutyl isobutyrate and 2,2,4,4-tetramethylcyclobutane-1,3-diol and 3-hydroxy-2,2,4,4-tetramethylcyclobutanone;

(2) optionally hydrogenating any unreacted 2,2,4,4-tetramethylcyclobutanedione and 3-hydroxy-2,2,4,4-tetramethylcyclobutanone to produce 2,2,4,4-tetramethylcyclobutane-1,3-diol;

(3) hydrolyzing the isobutyl isobutyrate optionally in the presence of an acid catalyst to produce isobutyric acid and isobutanol, and optionally wherein the isobutanol is optionally recycled to step (1);

(4) converting the isobutyric acid to 2,2,4,4-tetramethylcyclobutanedione, wherein the 2,2,4,4-tetramethylcyclobutanedione is optionally recycled to step (1).

4. The process according to claim 1, wherein the transfer hydrogenation catalyst is $((Ph_4C_4CO)_2H(\mu\text{-}H)(CO)_4Ru_2)$.

5. The process according to claim 1, wherein the conversion of the 2,2,4,4-tetramethylcyclobutanedione is at least 50%.

6. The process according to claim 1, wherein the conversion of the 2,2,4,4-tetramethylcyclobutanedione is at least 70%.

7. The process according to claim 1, wherein the conversion of the 2,2,4,4-tetramethylcyclobutanedione is at least 90%.

8. The process according to claim 1, wherein the selectivity of 2,2,4,4-tetramethylcyclobutane-1,3-diol is at least 30%.

9. The process according to claim 1, wherein the selectivity of 2,2,4,4-tetramethylcyclobutane-1,3-diol is at least 60%.

10. The process according to claim 1, wherein the process temperature ranges from about 50° C. to about 300° C.

11. The process according to claim 1, wherein the process temperature ranges from about 50° C. to about 200° C.

12. The process according to claim 1, wherein the process is under at least 200 psig of nitrogen pressure.

13. The process according to claim 1, wherein the process time is from 5 minutes to 5 hours.

14. The process according to claim 1, wherein the catalyst concentration is from about 0.001 mole percent to 10 mol percent based on the concentration of the 2,2,4,4-tetramethylcyclobutanedione.

15. The process according to claim 1, wherein the concentration of the isobutanol to 2,2,4,4-tetramethylcyclobutanedione is from a mole ratio of 1:1 to 50:1.

16. The process according to claim 1, wherein the concentration of the isobutanol to 2,2,4,4-tetramethylcyclobutanedione is from a mole ratio of 1:1 to 20:1.

17. The process according to claim 1, wherein the concentration of the isobutanol to 2,2,4,4-tetramethylcyclobutanedione is from a mole ratio of 1:1 to 10:1.

18. The process according to claim 1, wherein the concentration of the isobutanol to 2,2,4,4-tetramethylcyclobutanedione is from a mole ratio of 1:1 to 5:1.

19. A process for producing 2,2,4,4-tetramethylcyclobutane-1,3-diol with bio-content comprising:

(1) contacting 2,2,4,4-tetramethylcyclobutanedione with isobutanol comprising bio-isobutanol in the presence of a tandem transfer hydrogenation and Tischenko reaction catalyst to produce bio-isobutyl isobutyrate and bio-2,2,4,4-tetramethylcyclobutane-1,3-diol and bio-3-hydroxy-2,2,4,4-tetramethylcyclobutanone;

(2) optionally hydrogenating any unreacted bio-2,2,4,4-tetramethylcyclobutanedione and bio-3-hydroxy-2,2,4,4-tetramethylcyclobutanone to produce bio-2,2,4,4-tetramethylcyclobutane-1,3-diol;

(3) hydrolyzing the bio-isobutyl isobutyrate optionally in the presence of an acid catalyst to produce bio-isobutyric acid and bio-isobutanol, and optionally wherein the produced bio-isobutanol is optionally recycled to step (1);

(4) converting the bio-isobutyric acid to bio-2,2,4,4-tetramethylcyclobutanedione wherein the bio-2,2,4,4-tetramethylcyclobutanedione is optionally recycled to step (1).

20. The process of claim 19, wherein isobutanol comprises at least 25% bio-isobutanol; or at least 50% bio-isobutanol; or at least 75% bio-isobutanol.

* * * * *